(12) United States Patent
Choi et al.

(10) Patent No.: US 12,070,448 B2
(45) Date of Patent: Aug. 27, 2024

(54) USE OF CARBAMATE COMPOUND FOR PREVENTION, ALLEVIATION OR TREATMENT OF STATUS EPILEPTICUS

(71) Applicant: SK BIOPHARMACEUTICALS CO., LTD., Gyeonggi-do (KR)

(72) Inventors: Eun Ju Choi, Gyeonggi-do (KR); Hye Won Shin, Gyeonggi-do (KR); Yu Jin Shin, Gyeonggi-do (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 829 days.

(21) Appl. No.: 17/277,856

(22) PCT Filed: Sep. 20, 2019

(86) PCT No.: PCT/KR2019/012184
§ 371 (c)(1),
(2) Date: Mar. 19, 2021

(87) PCT Pub. No.: WO2020/060252
PCT Pub. Date: Mar. 26, 2020

(65) Prior Publication Data
US 2021/0346348 A1 Nov. 11, 2021

Related U.S. Application Data

(60) Provisional application No. 62/734,406, filed on Sep. 21, 2018.

(51) Int. Cl.
*A61K 31/41* (2006.01)
*A61P 25/08* (2006.01)

(52) U.S. Cl.
CPC ............... *A61K 31/41* (2013.01); *A61P 25/08* (2018.01)

(58) Field of Classification Search
CPC ................................. A61K 31/41; A61P 25/08
See application file for complete search history.

(56) References Cited

U.S. PATENT DOCUMENTS

| 7,598,279 B2 * | 10/2009 | Choi | ................. | A61P 25/20 |
| | | | | 548/255 |
| 10,456,376 B2 * | 10/2019 | Shin | ................. | A61K 9/28 |
| 11,389,429 B2 * | 7/2022 | Shin | ................. | A61K 9/0019 |

FOREIGN PATENT DOCUMENTS

| KR | 10-2008-0005437 A | 1/2008 |
| KR | 10-2018-0068493 A | 6/2018 |
| WO | WO-2005/023243 A1 | 3/2005 |
| WO | WO-2018111000 A1 | 6/2018 |

OTHER PUBLICATIONS

M. Bialer et al., Epilepsy Research, 2013, vol. 103, pp. 2-30.
Tenkan, Epilepsy Treatment Guideline, 2018, pp. 76-90.
International Search Report from corresponding PCT Application No. PCT/KR2019/012184, dated Dec. 30, 2019.
Bialer, M. et al. Progress report on new antiepileptic drugs: A summary of the Twelfth Eilat Conference (EILAT XII). Epilepsy Research 2015, vol. 11I, pp. 85-141.
Krauss, G. et al. Seizure Freedom with YKP3089 as Adjunctive Therapy for Refractory Partial-Onset Seizures in Double-Blind Placebo-Controlled Trials (P2, 019). Neurology.2016, vol. 86. 16 Supplement.

* cited by examiner

*Primary Examiner* — Golam M Shameem
(74) *Attorney, Agent, or Firm* — Harness, Dickey & Pierce, P.L.C.

(57) ABSTRACT

The present invention relates to a use for the purpose of preventing, alleviating, or treating status epilepticus by administering a medicament or pharmaceutical composition comprising a carbamate compound of chemical formula 1.

8 Claims, 7 Drawing Sheets

Seizure count when drug is administered immediately after onset of status epilepticus (Unpaired t test, ***: P < 0.0001, statistical significance in comparison with vehicle group)

Seizure score when drug is administered immediately after onset of status epilepticus (Unpaired t test, ***: P < 0.0001, statistical significance in comparison with vehicle group)

Mortality when drug is administered immediately after onset of status epilepticus Seizure count when drug is administered 10 minutes after onset of status epilepticus (One-way ANOVA, post-hoc: Tukey's multiple comparisons test
**: $P < 0.01$, statistical significance in comparison with vehicle group)

Seizure score when drug is administered 10 minutes after onset of status epilepticus (One-way ANOVA, post-hoc: Tukey's multiple comparisons test
***: $P < 0.001$, statistical significance in comparison with vehicle group)

USE OF CARBAMATE COMPOUND FOR PREVENTION, ALLEVIATION OR TREATMENT OF STATUS EPILEPTICUS

CROSS-REFERENCE TO RELATED APPLICATIONS

This application is a national phase application of PCT Application No. PCT/KR2019/012184, filed on Sep. 20, 2019, which claims priority to U.S. Provisional Application No. 62/734,406, filed on Sep. 21, 2018. The entire disclosure of the applications identified in this paragraph is incorporated herein by reference.

TECHNICAL FIELD

The present invention relates to use of a carbamate compound of the following Formula 1 for the purpose of preventing, alleviating or treating status epilepticus by administering a medicament or a pharmaceutical composition comprising said carbamate compound:

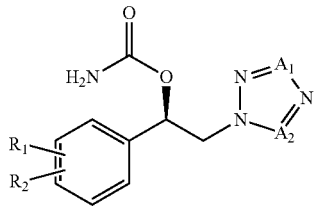

[Formula 1]

wherein,
$R_1$, $R_2$, $A_1$ and $A_2$ are as defined herein.

BACKGROUND ART

Status epilepticus (SE) refers to seizures that last more than 5 minutes or occur continuously without recovery of consciousness. The annual incidence of status epilepticus is 41 out of 100,000, with a mortality rate of about 20% (Trinka, E., Höfler, J. and Zerbs, A. (2012), Causes of status epilepticus. Epilepsia, 53:127-138). As the duration of status epilepticus increases, patients do not respond to the treatment drugs and the prognosis is poor because the neuronal damage becomes more severe. Accordingly, it is recommended to start treatment immediately.

Status epilepticus may occur in patients already suffering from epilepsy—for example, it may be caused by low antiepileptic drug (AED) level in patients already suffering from epilepsy. In addition, other causes of status epilepticus may include stroke, metabolic derangements, central nervous system (CNS) infections, traumatic brain injury, alcohol abuse, brain tumors, chronic cerebral infarction lesions and the like. Therefore, even if the efficacy of a compound is shown in a model of epilepsy or a patient suffering from epilepsy, it is not necessarily possible to expect the efficacy of the compound for status epilepticus from this.

Status epilepticus can be divided into convulsive status epilepticus and non-convulsive status epilepticus. In the case of convulsive status epilepticus, continuous tonic-clonic seizure occurs, a second seizure occurs without recovery of consciousness, followed by repeated seizures. Since convulsive status epilepticus can be life-threatening, immediate medical treatment is required after symptoms occur. Non-convulsive status epilepticus is cases where complex partial seizures (focal impaired awareness) and simple partial non-convulsive status epilepticus are sustained and repeated. In the case of non-convulsive status epilepticus, it is difficult to detect the occurrence of symptoms because patients do not completely lose consciousness such as convulsive status epilepticus. Electroencephalography (EEG) should be performed first for the diagnosis of symptoms. Patients with non-convulsive status epilepticus are at risk of developing convulsive status epilepticus, and in this case, emergency treatment is also required.

Treatment of status epilepticus is to alleviate the continuous seizure clinically and on brain waves. There are stages depending on the time elapsed after the occurrence of status epilepticus and the response to treatment, and as the initial first-line medicaments after the onset of symptoms, benzodiazepines (BDZs), such as diazepam, midazolam and lorazepam are mainly used to stop status epilepticus by intravenous injection. If status epilepticus does not stop with the first-line medicament, anti-epileptic drugs are used as second-line medicaments. Not all anti-epileptic drugs are active on status epilepticus, and among various anti-epileptic drugs, phenobarbital, phenytoin, valproic acid, levetiracetam and lacosamide are used in the treatment of status epilepticus. When status epilepticus persists for more than 40 minutes on clinical observation or electroencephalography even after administration of the second-line medicament, it is called a refractory status epilepticus stage. At this stage, there are no clear treatment guidelines, but repeated administration of second-line medicaments or high-dose administration of general anesthetics such as propofol is used in combination with electroencephalography (Glauser T, Shinnar S, Gloss D, et al. Evidence-Based Guideline: Treatment of Convulsive Status Epilepticus in Children and Adults: Report of the Guideline Committee of the American Epilepsy Society. *Epilepsy Curr.* 2016; 16(1):48-61).

As such, various drug treatment methods have been used for the treatment of status epilepticus, but a satisfactory level of effect is not obtained, or restrictions on use still exist due to side effects, so there is a need for new drugs with improved efficacy and fewer side effects.

Meanwhile, U.S. Pat. No. 7,598,279 discloses azole compounds useful for the treatment of epilepsy. However, the above patent does not disclose the use of this compound for the prevention, alleviation or treatment of status epilepticus.

SUMMARY

Problem to be Solved

The present invention is intended to provide a method for the prevention, alleviation or treatment of status epilepticus. In addition, the present invention is intended to provide the use of a carbamate compound of the following Formula 1, or a pharmaceutically acceptable salt, solvate or hydrate thereof, for the prevention, alleviation or treatment of status epilepticus:

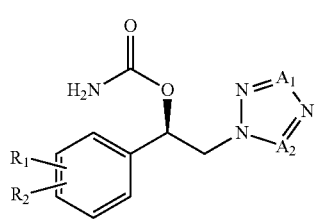

[Formula 1]

wherein,
$R_1$, $R_2$, $A_1$ and $A_2$ are as defined herein.

Technical Solution to the Problem

The present invention provides a medicament for the prevention, alleviation or treatment of status epilepticus, comprising a therapeutically effective amount of a carbamate compound of the following Formula 1, or a pharmaceutically acceptable salt, solvate or hydrate thereof:

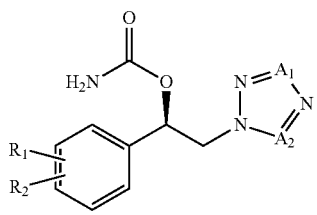

[Formula 1]

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

In addition, the present invention provides a pharmaceutical composition for the prevention, alleviation or treatment of status epilepticus, comprising a therapeutically effective amount of the carbamate compound of the above Formula 1, or a pharmaceutically acceptable salt, solvate or hydrate thereof; and further one or more of a pharmaceutically acceptable carrier.

In addition, the present invention provides a method for preventing, alleviating or treating status epilepticus in a subject, comprising administering to the subject a therapeutically effective amount of the carbamate compound of the above Formula 1, or a pharmaceutically acceptable salt, solvate or hydrate thereof.

In addition, the present invention provides the use of the carbamate compound of the above Formula 1, or a pharmaceutically acceptable salt, solvate or hydrate thereof for the prevention or treatment of status epilepticus, or for the improvement of symptoms associated therewith.

According to one embodiment of the present invention, in the above Formula 1, $R_1$ and $R_2$ are each independently selected from the group consisting of hydrogen, halogen and $C_1$-$C_8$ alkyl.

In one embodiment of the present invention, the halo-$C_1$-$C_8$ alkyl is perfluoroalkyl.

According to another embodiment of the present invention, the carbamate compound of the above Formula 1 is carbamic acid (R)-1-(2-chlorophenyl)-2-tetrazol-2-yl-ethyl ester of the following Formula 2:

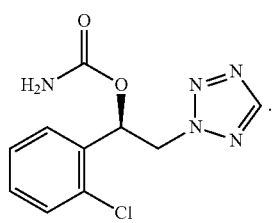

[Formula 2]

A person having ordinary skill in the art of synthesis of compounds could have easily prepared the carbamate compounds of the above Formulas 1 and 2 using known compounds or compounds which can be easily prepared therefrom. Specifically, methods for preparing the compounds of the above Formula 1 are described in detail in International Publication Nos. WO 2006/112685 A1, WO 2010/150946 A1 and WO 2011/046380 A2, the disclosures of which are incorporated herein by reference. The compounds of the above Formula 1 can be chemically synthesized by any of the methods described in the above documents, but the methods are merely exemplary ones, and the order of the unit operation and the like may be selectively changed if necessary. Hence, the above methods are not intended to limit the scope of the invention.

The carbamate compounds of the above Formula 1 can be used for the prevention, alleviation or treatment of status epilepticus.

According to one embodiment of the present invention, status epilepticus can be divided into convulsive status epilepticus and non-convulsive status epilepticus. In the case of convulsive status epilepticus, continuous tonic-clonic seizure occurs, a second seizure occurs without recovery of consciousness, followed by repeated seizures. Since convulsive status epilepticus can be life-threatening, immediate medical treatment is required after symptoms occur. Non-convulsive status epilepticus is cases where complex partial seizures (focal impaired awareness) and simple partial non-convulsive status epilepticus are sustained and repeated.

According to one embodiment of the present invention, status epilepticus may be caused by one or more selected from stroke, metabolic derangements, CNS infections, traumatic brain injury, alcohol abuse, brain tumors, chronic cerebral infarction lesions and low antiepileptic drug (AED) level in patients who already suffer from epilepsy.

According to one embodiment of the present invention, the status epilepticus may be convulsive status epilepticus or non-convulsive status epilepticus.

According to one embodiment of the present invention, the carbamate compounds of the above Formula 1 may be used as a second-line medicament for the prevention, alleviation or treatment of status epilepticus. According to one embodiment of the present invention, (a) the carbamate compound of the above Formula 1 may be used as a combination with (b) an additional active agent—for example, benzodiazepine-based drugs or anti-epileptic drugs, preferably one or more drugs selected from the group consisting of diazepam, midazolam, lorazepam, phenobarbital, phenytoin, valproic acid, levetiracetam and lacosamide. The term "combination" means that two or more drugs are used together, but does not mean a state in which two or more drugs are necessarily mixed. Two or more drugs may be present together in a single preparation in a mixed state, or may be used as separate preparations. That is, "combination" includes both a single preparation and two separate preparations, so it can be administered simultaneously, separately or sequentially.

According to another embodiment of the present invention, in the combination the weight ratio (a:b) of the ingredient (a) and the ingredient (b) may be within the scope of 1,000:1 to 1:1,000. According to still another embodiment of the present invention, in the combination the weight ratio (a:b) of the ingredient (a) and the ingredient (b) may be within the scope of 100:1 to 1:100.

According to still another embodiment of the present invention, the combination may comprise the compound of Formula 1 in an amount of 12.5 mg to 500 mg, based on the free form.

A status epilepticus model refers to an in vivo or in vitro model system representing at least one aspect or element of status epilepticus, and allows the evaluation of anti-status epilepticus medicaments.

In one embodiment, a patch clamp model may be useful for analyzing the efficacy of anti-status epilepticus medicaments. Through high-frequency epileptiform discharges obtained by similarly realizing cranial nerve activity at the occurrence of status epilepticus in laboratory conditions, it is possible to directly check whether the test compound is effective in the status epilepticus model (Deshpande L S, Lou J K, Mian A, Blair R E, Sombati S, DeLorenzo R J. In vitro status epilepticus but not spontaneous recurrent seizures cause cell death in cultured hippocampal neurons. *Epilepsy Res.* 2007; 75(2-3):171-179. doi:10.1016/j.eplepsyres.2007.05.011).

In one embodiment, the status epilepticus model may be selected from chemical (e.g., pilocarpine)-induced status epilepticus, electrical-induced status epilepticus, an in vitro model (low magnesium in brain slice) and the like.

In the chemical-induced in vivo status epilepticus model, status epilepticus is induced by intraparietal injection of substances that cause status epilepticus (e.g., pilocarpine, kainic acid, lithium-pilocarpine, flurothyl, etc.) into the rostral part of the back of a mouse or rat. After injection of status epilepticus-inducing substance, the behaviors of experimental animals were observed according to the Racine score, and the number of seizures and mortality are measured. The test compound can be administered intraperitoneally or by other routes after induction of status epilepticus, and the efficacy of the test compound can be compared to the positive control compound.

According to one embodiment of the present invention, the carbamate compounds of the above Formula 1 can be used for the prevention, alleviation or treatment of refractory status epilepticus.

"Refractory status epilepticus" means when status epilepticus persists for more than 40 minutes on clinical observation or electroencephalography even after administration of the second-line medicament.

The dosage of the carbamate compound of Formula 1 for the prevention, alleviation or treatment of the above diseases may typically vary depending on the severity of the disease, the body weight and the metabolic status of the subject. A "therapeutically effective amount" for an individual patient refers to an amount of the active compound sufficient to achieve the above pharmacological effect—i.e., the therapeutic effect as described above. The therapeutically effective amount of the compound of Formula 1 is 50 to 500 mg, 50 to 400 mg, 50 to 300 mg, 100 to 400 mg, 100 to 300 mg, 50 to 200 mg or 100 to 200 mg, based on the free form and once-daily administration to humans. It is preferably 50 to 300 mg, more preferably 50 to 200 mg.

The compound of the present invention may be administered by any conventional method used for administration of a therapeutic agent, such as oral, parenteral, intravenous, intramuscular, subcutaneous or rectal administration.

The medicament or pharmaceutical composition according to one embodiment of the present invention may comprise a therapeutically effective amount of a compound selected from the group consisting of the carbamate compounds of the present invention, their pharmaceutically acceptable salts, solvates, hydrates and combinations thereof.

Examples of the pharmaceutically acceptable salts of the carbamate compounds of the above Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydravamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemisuccinate, sulfate or hemi-sulfate, tannate, tartrate, oxalate or hemi-tartrate, teoclate, triethiodide, benzathine, chloroprocaine, choline, diethanolamine, ethylenediamine, meglumine, procaine, aluminum, ammonium, tetramethylammonium, calcium, lithium, magnesium, potassium, sodium and zinc.

The medicament or pharmaceutical composition according to one embodiment of the present invention may be administered orally or parenterally.

The parenteral administration may include intravenous injection, subcutaneous injection, intramuscular injection, intraperitoneal injection, endothelial administration, topical administration, intranasal administration, intravaginal administration, intrapulmonary administration, rectal administration and the like. In one embodiment of the present invention, the parenteral administration may be in a form of a parenteral liquid formulation. The liquid formulation means a preparation in which the active ingredient is dissolved in a solvent such as water. The parenteral liquid formulation may be an injection formulation. Sterile water may be used as a solvent being water. Saline solution, PBS buffer, isotonic water, Ringers lactate solution, 5% dextrose in water and the like can be used as a solvent other than water. Known solvents used in the manufacture of medicines can be suitably used. The parenteral liquid formulation may further contain an additive. Any additives that are commonly used in parenteral liquid formulation in the field of pharmaceutical preparations can be suitably used. Specifically, additives include isotonic agents, stabilizers, buffers, preservatives and the like. Examples of isotonic agents include sugars such as glucose, sorbitol and mannitol, sodium chloride and the like. Examples of stabilizers include sodium sulfite and the like. In addition, the parenteral liquid formulation has a pH suitable for administration to the human body without adding a pH adjusting agent, and no significant pH change is observed under the storage conditions. Therefore, a pH adjusting agent may or may not be added to the parenteral liquid formulation. If the pH adjusting agent is not added, the manufacturing process can be simplified, and it is advantageous that there is no need to consider compatibility with the pH adjusting agent. Usable buffers include a borate buffer, a phosphate buffer, a citrate buffer, a tartrate buffer and the like. Examples of preservatives include parabens (methyl, ethyl, propyl and butyl paraben), paraben sodium salts, potassium sorbate, sodium benzoate and sorbic acid.

In the case of oral administration, the pharmaceutical composition according to one embodiment of the present invention may be formulated as a plain tablet (uncoated tablet) or such that the active agent is coated or is protected against degradation in the stomach. In addition, the composition can be administered by any device capable of transferring the active substance to a target cell. The route of administration may vary depending upon the general condition and age of the subject to be treated, the nature of the treatment condition and the active ingredient selected.

A suitable dosage of the medicament or pharmaceutical composition according to one embodiment of the present invention may vary depending on factors such as the formulation method, administration method, age, body weight and gender of patients, pathological condition, diet, administration time, administration route, excretion rate and reaction sensitivity, and doctors having ordinary skill can easily determine and prescribe dosages that are effective for the desired treatment or prophylaxis. The pharmaceutical composition according to one embodiment may be administered in one or more doses, for example, one to four times per day. The pharmaceutical composition according to one embodiment may contain the compounds of Formula 1 in the amount of 50 to 500 mg, 50 to 400 mg, 50 to 300 mg, 100 to 400 mg, 100 to 300 mg, 50 to 200 mg or 100 to 200 mg, preferably 50 to 300 mg, more preferably 50 to 200 mg, based on the free form.

The medicament or pharmaceutical composition according to one embodiment of the present invention may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet, or a capsule, and may further include a dispersing or stabilizing agent. In addition, the pharmaceutical composition may be administered in the form of suppositories, sprays, ointments, creams, gels, inhalants or skin patches. The pharmaceutical composition may also be prepared for mammalian administration, more preferably for human administration.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivatives (e.g., microcrystalline cellulose) or mixtures thereof.

In one embodiment, suitable binders include, but are not limited to, povidone, copovidone, methylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, silica, colloidal silicon dioxide, talc and the like.

In one embodiment, suitable lubricants include, but are not limited to, long chain fatty acids and salts thereof, such as magnesium stearate and stearic acid, talc, glyceride wax or mixtures thereof.

As used herein, the terms "prevent," "preventing" and "prevention" refer to reducing or eliminating the likelihood of a disease.

As used herein, the terms "alleviate," "alleviating" and "alleviation" refer to ameliorating a disease and/or its accompanying symptoms altogether or in part.

As used herein, the terms "treat," "treating" and "treatment" refer to eliminating a disease and/or its accompanying symptoms altogether or in part.

As used herein, the term "subject" refers to an animal that is the object of therapy, observation or experiment, preferably a mammal (such as primates (e.g., a human), cattle, sheep, goats, horses, dogs, cats, rabbits, rats, mice, etc.), most preferably a human.

As used herein, the term "therapeutically effective amount" refers to the amount of active compound or pharmaceutical formulation that elicits a biological or medical response in the system, animal or human, including alleviation of the symptoms of the disease or disorder to be treated, wherein said amount is sought by a researcher, veterinarian, doctor (physician) or other clinician.

As used herein, the term "composition" encompasses a product that contains a specified amount of a particular ingredient and any product that results directly or indirectly from a combination of specified amounts of particular ingredients.

Effect of the Invention

The medicament and the pharmaceutical composition according to the present invention can effectively prevent, alleviate and treat status epilepticus without side effects in comparison with conventional therapeutic agents.

DETAILED DESCRIPTION

Hereinafter, the present invention will be explained in more detail through working examples. However, the following working examples are only intended to illustrate one or more embodiments and are not intended to limit the scope of the invention.

Preparation Example: Synthesis of Carbamic Acid (R)-1-(2-chlorophenyl)-2-tetrazol-2-yl-ethyl Ester Carbamic acid (R)-1-(2-chlorophenyl)-2-tetrazol-2-yl-ethyl ester (hereinafter referred to as "Test Compound") was prepared according to the method described in Preparation Example 50 of International Publication No. WO 2010/150946.

Example 1: Inhibitory Effect Against Status Epilepticus Using Whole-Cell Patch-Clamp Model in Mouse Hippocampus Experimental Animals Male mice (C57BL/6, 24-26 g) were used. The experimental animals were housed under a 12-hour light/dark cycle (lighting from 7 pm to 7 am) and maintained at a temperature of 22-25° C. and about 40 to 60% relative humidity. Food and water were provided ad libitum.

Preparation of Hippocampal Slice

For whole-cell patch-clamp recording, the brain of the mouse was excised, and the hippocampal slices (310 mm) were prepared with oxygenated artificial cerebrospinal fluid (ACSF) (124 mM NaCl, 3.0 mM KCl, 1.23 mM $NaH_2PO_4$, 2.2 mM $CaCl_2$, 1.2 mM $MgCl_2$, 26 mM $NaHCO_3$, and 10 mM glucose, pH 7.4). All experiments were performed in visually guided CA1 pyramidal neurons, and a glass pipette (4-5 MΩ) was used for recording. After incubating the tissue for 1 hour, a single slice was submerged in a recording chamber and continuously superfused with oxygenated artificial cerebrospinal fluid (32° C.; 95% $O_2$/5% $CO_2$).

For low $Mg^{2+}$-induced seizure-like events (SLEs) measurement, 0 mM $MgCl_2$ and 5.0 mM KCl were used. SLEs were defined by more than three spikes in a burst. Whole-cell patch-clamp currents were digitized with a MultiClamp 700B amplifier and a Digidata 1440 (Axon Instruments, CA), and the acquired data were analyzed with the pCLAMP version 10.2 (Axon Instruments) and the Mini Analysis Program (Synaptosoft).

SLEs Measurement Protocols

Early SLEs (immediately after onset of SLEs): measurement of SLEs observed 20-30 minutes after the application of low $Mg^{2+}$ ACSF.

Late SLEs (after 1 hour incubation in low $Mg^{2+}$ ACSF): measurement of SLEs observed immediately after whole-cell rupture.

The treatment of the compound for measuring the effect of Test Compound was initiated 10-15 minutes after the occurrence of SLEs.

Statistics

The effect of Test Compound was a comparison value (%) to the SLE value that occurred after the treatment of low $Mg^{2+}$ ACSF and before the treatment of Test Compound, and was represented as the mean±standard error. When there was a difference of $p<0.05$ in data by using Student's t-test, statistical significance was recognized.

Figure 1:
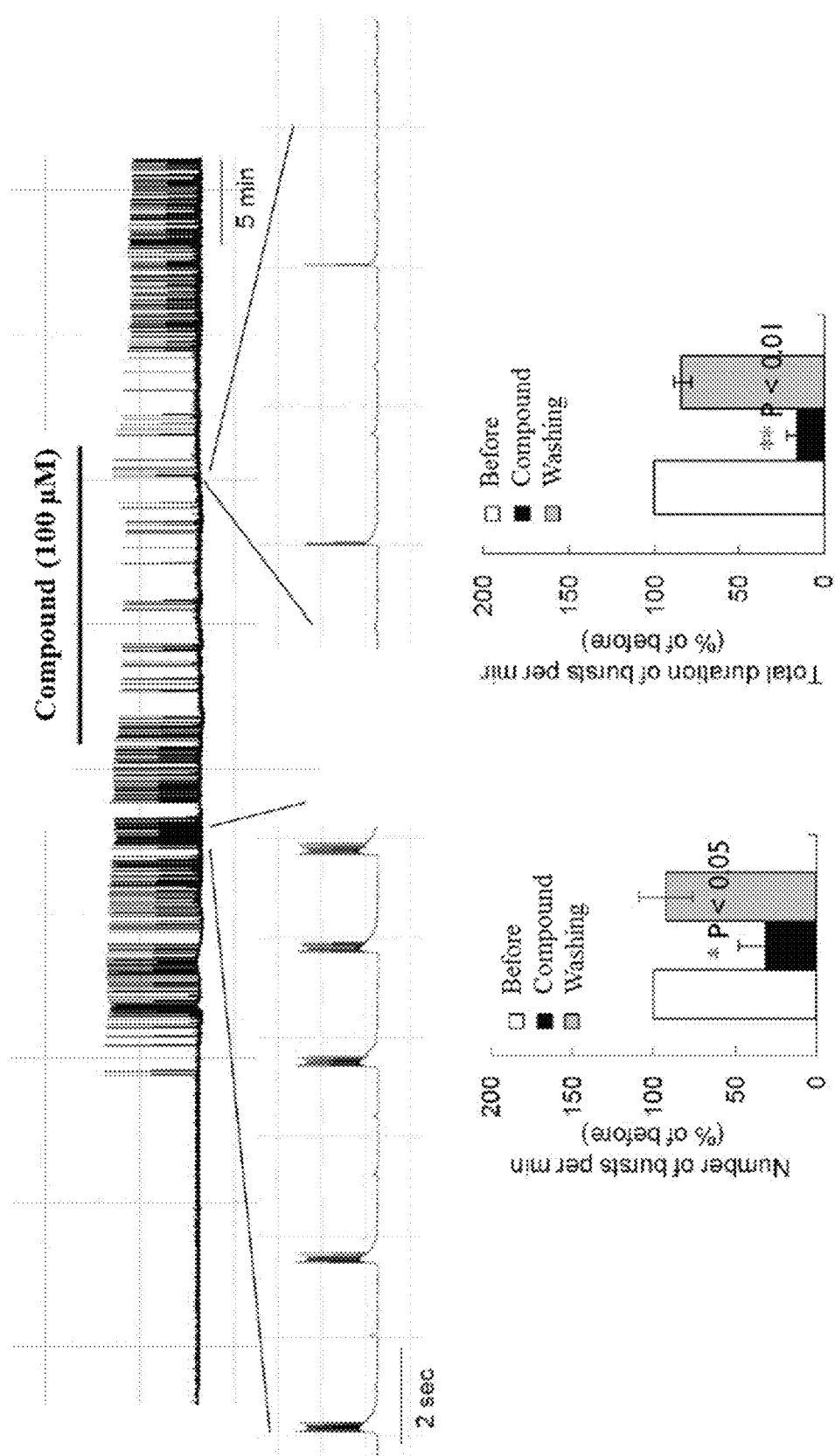
FIG. 1 and FIG. 2 show the results of experiments on the effect of inhibiting status epilepticus in vitro using a whole-cell patch-clamp model in the mouse hippocampus. It is the result of comparing the change of signals of seizure-like burst spikes when Test Compound is treated and after Test Compound is washed out at early seizure-like events (SLEs) (FIG. 1) and late SLEs (FIG. 2). (Before: before Test Compound treatment, Compound: during Test Compound treatment, Washing: after Test Compound washing)
Figure 2:
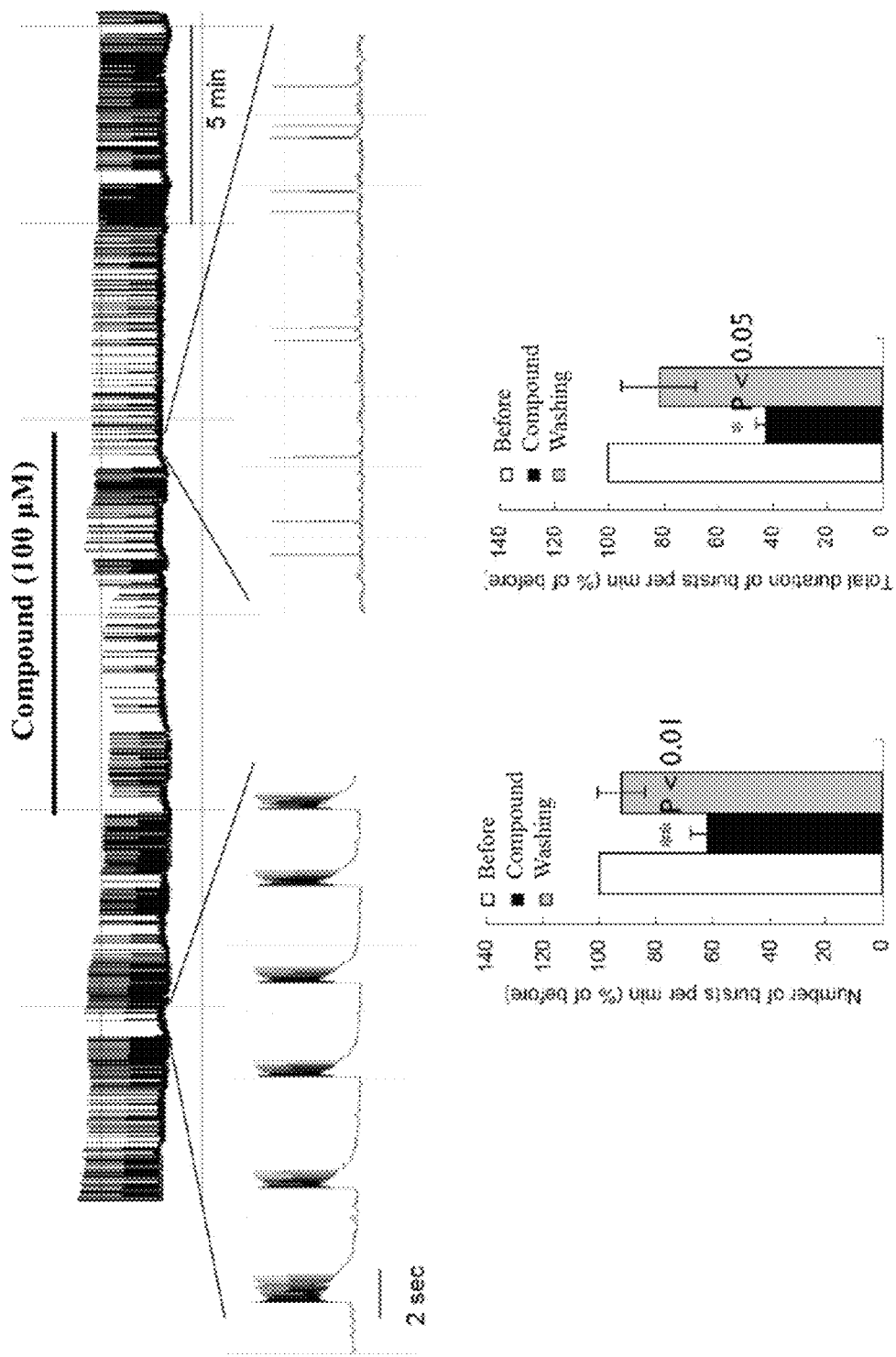
Figure 3:
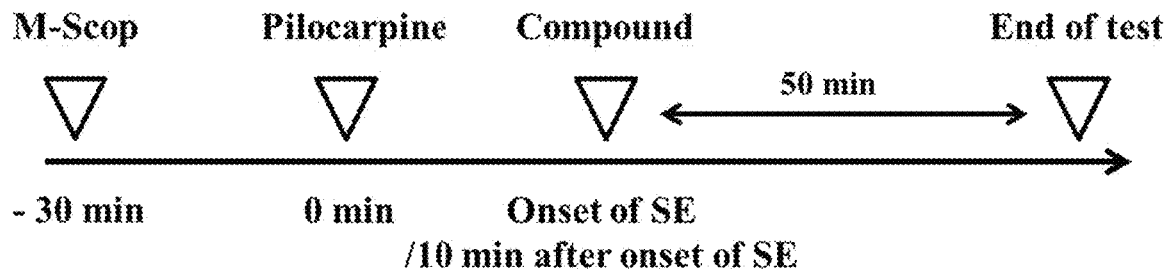
FIG. 3 is a scheme of an experiment inducing status epilepticus by administering pilocarpine.

As can be seen from FIG. 1 (early SLEs, n=5) and FIG. 2 (late SLEs, n=8), when 100 μM of Test Compound was treated 10-15 minutes after the occurrence of SLE, the number and duration of SLE were significantly reduced compared to after washing of Test Compound. The values compared to the degree of SLE occurrence before treatment with Test Compound are represented in Table 1.

TABLE 1

|  | Number of SLE in comparison with before treatment of Test Compound | | | Duration of SLE in comparison with before treatment of Test Compound | | |
| --- | --- | --- | --- | --- | --- | --- |
|  | During treatment | After washing | t-Test result | During treatment | After washing | t-Test result |
| Early SLE | 31.45 ± 16.13% | 91.99 ± 16.47% | P < 0.05 | 15.39 ± 6.82% | 83.63 ± 5.14% | P < 0.01 |
| Late SLE | 62.12 ± 5.59% | 92.36 ± 8.21% | P < 0.01 | 42.61 ± 3.50% | 81.81 ± 13.78% | P < 0.05 |

As above, Test Compound showed a statistically significant effect in an in vitro model of $Mg^{2+}$-induced seizure-like activity.

Example 2: Inhibitory Effect Against Status Epilepticus Using Pilocarpine Induced Status Epilepticus Experimental Animals Male mice (C57BL/6, 21-24 g) were used. The experimental animals were housed under a 12-hour light/dark cycle (lighting from 7 pm to 7 am) and maintained at a temperature of 22-25° C. and about 40 to 60% relative humidity. Food and water were provided ad libitum. The animals were randomly divided into the following groups.

Experimental Groups of Administering Test Compound Immediately after Onset of Status Epilepticus
   10 Mice intraperitoneally single administered with 30% PEG300 as a control vehicle at a volume of 10 m/kg
   9 Mice intraperitoneally single administered Test Compound at a dose of 20 mg/kg (10 ml/kg)

Experimental Groups of Administering Positive Control and Test Compound 10 Minutes after Onset of Status Epilepticus
   As a control, 13 mice intraperitoneally single administered with 30% PEG300 (vehicle) at a volume of 10 ml/kg
   As a positive control, 12 mice intraperitoneally single administered valproic acid (VPA) at a dose of 200 mg/kg (10 ml/kg)
   13 Mice intraperitoneally single administered Test Compound at a dose of 25 mg/kg (10 ml/kg)

Induction of Status Epilepticus

Methylscopolamine was dissolved in a vehicle (0.9% saline) at a concentration of 1 mg/kg (10 m/kg) and administered subcutaneously to the back of the neck. After 30 minutes, pilocarpine was dissolved in a vehicle (0.9% saline) at a concentration of 320 mg/kg (10 ml/kg) and administered intraperitoneally.

Measurement of Status Epilepticus Behavior

In the experimental group of drug-administering immediately after onset of status epilepticus, animal behaviors were observed after the administration of drugs immediately after onset of status epilepticus in which the animals' continuous tonic-clonic seizure behavior and the number of occurrences were observed for 50 minutes according to the modified Racine score (Ronald J Racine, Modification of seizure activity by electrical stimulation: II. Motor seizure, Electroencephalography and Clinical Neurophysiology: II., Volume 32, Issue 3, 1972, Pages 281-294).

In the case of the drug-administered experimental groups 10 minutes after onset of status epilepticus, valproic acid and Test Compound were administered 10 minutes after onset of status epilepticus. Then, the animals' continuous tonic-clonic seizure behavior and the number of occurrences were observed for 50 minutes according to the modified Racine score (Ronald J Racine, Modification of seizure activity by electrical stimulation: II. Motor seizure, Electroencephalography and Clinical Neurophysiology: II., Volume 32, Issue 3, 1972, Pages 281-294).

Administration

In the experimental groups of drug-administering immediately after onset of status epilepticus, Test Compound was administered intraperitoneally at a dose of 20 mg/kg (10 ml/kg).

In the case of the drug-administered experimental groups 10 minutes after onset of status epilepticus, Test Compound was administered intraperitoneally at a dose of 25 mg/kg (10 ml/kg). At the same time point, valproic acid (positive control group) was administered intraperitoneally at a dose of 200 mg/kg (10 ml/kg).

Statistics

In the experimental groups of drug-administering immediately after onset of status epilepticus, the effects of compound were represented as the mean±standard error. When there was a difference of p<0.05 in data by using t-test, statistical significance was recognized.

In the case of the drug-administered experimental groups 10 minutes after onset of status epilepticus, the effects of the compound were represented as the mean±standard error, and statistical significance was recognized when there was a difference of p<0.05 in data using one-way ANOVA and a Tukey's test as a post-hoc test.

Figure 4:
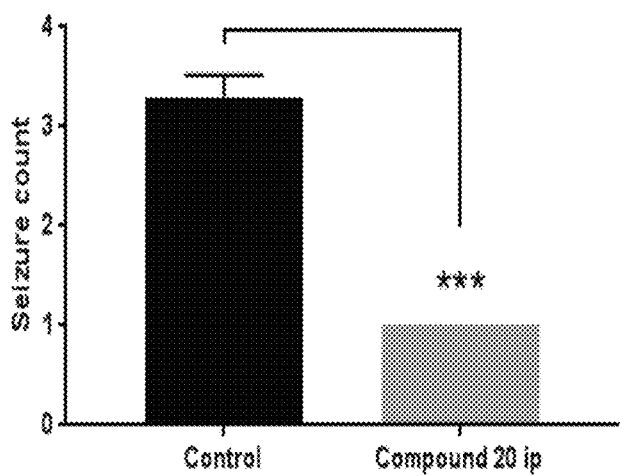
FIG. 4, FIG. 5 and FIG. 6 show the result of comparing the effects on reducing seizure count, seizure score and mortality in comparison with the control group (vehicle) for 50 minutes after administering Test Compound to the mouse that caused status epilepticus by administering pilocarpine.
Figure 5:
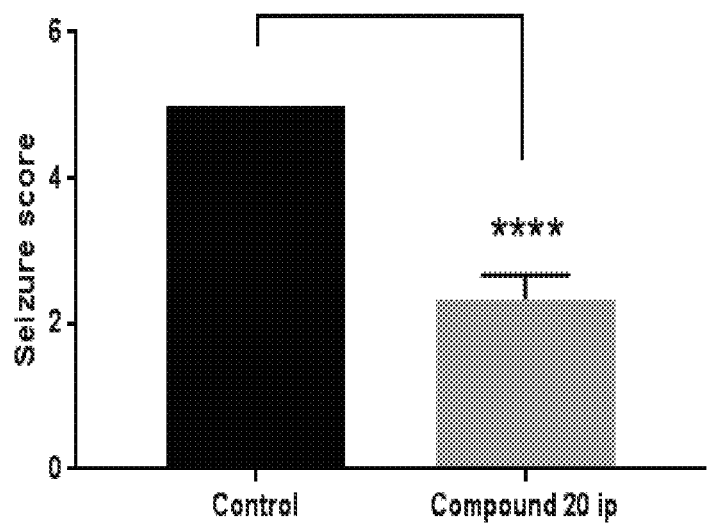
Figure 6:
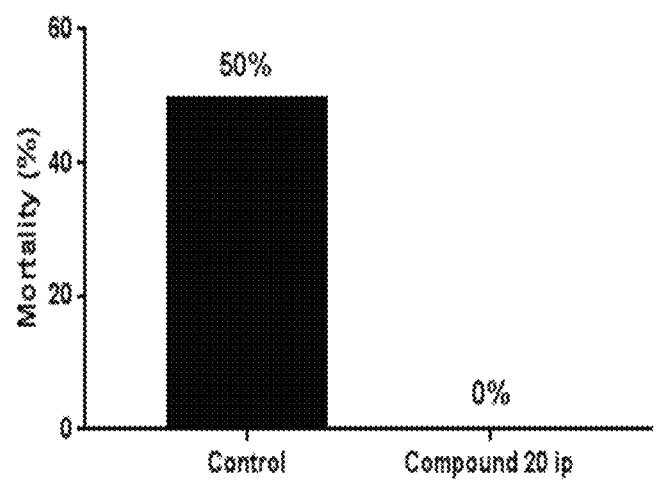

As can be seen from FIGS. 4, 5 and 6, when Test Compound was administered at a dose of 20 mg/kg immediately after the occurrence of status epilep-ticus, the number and score of pilocarpine-induced status epilepticus were statistically significantly suppressed compared to the control group, and the tendency to suppress mortality was also confirmed.

Figure 7:
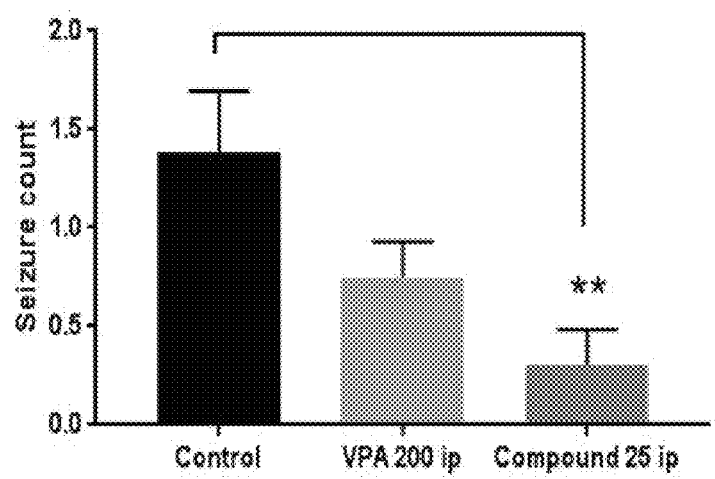
FIG. 7 and FIG. 8 show the result of comparing the effects on reducing seizure count and seizure score in comparison with the control group (vehicle) and the positive control group for 50 minutes after administering the test compound after the occurrence of status epilepticus to the mouse that caused status epilepticus by administering pilocarpine.
Figure 8:
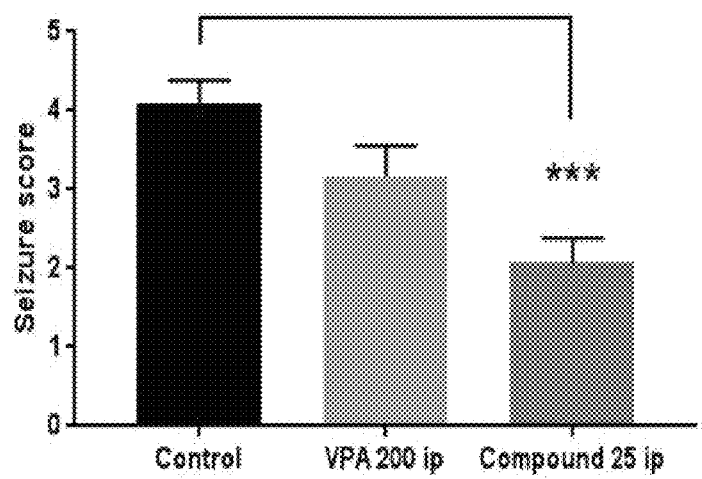

As can be seen from FIGS. 7 and 8, when Test Compound was administered intraperitoneally at a dose of 25 mg/kg 10 minutes after onset of status epilepticus, the number and score of pilocarpine-induced status epilepticus were statistically significantly suppressed compared to the control group.

TABLE 2

|  | Drug administration immediately after onset of status epilepticus | | | Drug administration 10 min after onset of status epilepticus | | | |
|---|---|---|---|---|---|---|---|
|  | Control group | Test Compound | t-test result | Control group | Positive control group | Test Compound | One-way ANOVA result |
| Seizure count | 3.3 ± 0.21 | 1.0 ± 0.00 | P < 0.0001 | 1.4 ± 0.31 | 0.8 ± 0.18 | 0.3 ± 0.17 | P < 0.01 |
| Seizure score | 5.0 ± 0.00 | 2.3 ± 0.33 | P < 0.0001 | 4.1 ± 0.31 | 3.2 ± 0.39 | 2.1 ± 0.31 | P < 0.001 |
| Mortality | 50% | 0% | — | 36% | 14% | 0% | — |

As above, Test Compound showed a statistically significant effect in a pilocarpine-induced status epilepticus animal model.

From the above results, it was confirmed that Test Compound showed significant effects on the status epilepticus model, and thus can be usefully used as a drug for the treatment of status epilepticus.

What is claimed is:

1. A method for alleviating or treating status epilepticus, comprising:
    administering to a subject in need thereof a therapeutically effective amount of a compound of Formula 1, or a pharmaceutically acceptable salt, solvate or hydrate thereof:

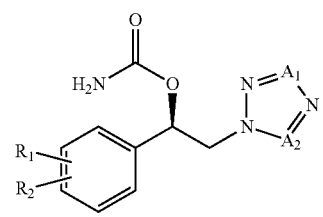

[Formula 1]

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and
one of $A_1$ and $A_2$ is CH, and the other is N.

2. The method according to claim 1, wherein $R_1$ and $R_2$ are each independently selected from the group consisting of hydrogen, halogen and $C_1$-$C_8$ alkyl.

3. The method according to claim 1, wherein the carbamate compound of Formula 1 is carbamic acid (R)-1-(2-chlorophenyl)-2-tetrazol-2-yl-ethyl ester of the following Formula 2:

[Formula 2]

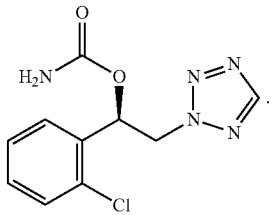

4. The method according to claim 1, wherein status epilepticus is caused by one or more selected from stroke, metabolic derangements, CNS infections, traumatic brain injury, alcohol abuse, brain tumors, chronic cerebral infarction lesions and low antiepileptic drug (AED) level in patients who already suffer from epilepsy.

5. The method according to claim 1, wherein the status epilepticus is convulsive status epilepticus.

6. The method according to claim 1, wherein the status epilepticus is non-convulsive status epilepticus.

7. The method according to claim 1, which is for mammalian administration.

8. The method according to claim 1, wherein the therapeutically effective amount of the carbamate compound of Formula 1 is 50 to 500 mg based on the free form once-daily administration.

* * * * *